United States Patent
Cambier et al.

(10) Patent No.: US 8,784,401 B2
(45) Date of Patent: Jul. 22, 2014

(54) STEERABLE CATHETER DEVICE AND METHOD FOR THE CHEMOEMBOLIZATION AND/OR EMBOLIZATION OF VASCULAR STRUCTURES, TUMOURS AND/OR ORGANS

(76) Inventors: Bernard Alfons lucie B. Cambier, Sint-Martens-Latem (BE); Anne Sophie Cecile M. L. De Wulf, Sint-Martens-Latem (BE)

(*) Notice: Subject to any disclaimer, the term of this patent is extended or adjusted under 35 U.S.C. 154(b) by 529 days.

(21) Appl. No.: 12/308,851

(22) PCT Filed: Jun. 30, 2006

(86) PCT No.: PCT/IB2006/002209
§ 371 (c)(1),
(2), (4) Date: Mar. 10, 2009

(87) PCT Pub. No.: WO2008/004018
PCT Pub. Date: Jan. 10, 2008

(65) Prior Publication Data
US 2009/0275878 A1 Nov. 5, 2009

(51) Int. Cl.
*A61M 25/00* (2006.01)
*A61M 31/00* (2006.01)
*A61M 29/00* (2006.01)
*A61N 1/30* (2006.01)

(52) U.S. Cl.
USPC ...... 604/528; 604/510; 604/93.01; 604/96.01; 604/21

(58) Field of Classification Search
USPC ........... 604/20, 21, 36, 48, 264, 96.01, 93.01, 604/508, 510, 528; 606/41
See application file for complete search history.

(56) References Cited

U.S. PATENT DOCUMENTS

| 5,462,544 A | 10/1995 | Saksena | |
|---|---|---|---|
| 6,254,598 B1 | 7/2001 | Edwards | |
| 6,652,515 B1 * | 11/2003 | Maguire et al. | 606/41 |
| 2002/0087156 A1 * | 7/2002 | Maguire et al. | 606/41 |
| 2002/0198521 A1 | 12/2002 | Maguire | |
| 2007/0083193 A1 * | 4/2007 | Werneth et al. | 606/41 |
| 2007/0129717 A1 * | 6/2007 | Brown et al. | 606/41 |
| 2008/0015569 A1 * | 1/2008 | Saadat et al. | 606/41 |

FOREIGN PATENT DOCUMENTS

| EP | 0928601 | 7/1999 |
|---|---|---|
| EP | 1502624 | 2/2005 |

* cited by examiner

*Primary Examiner* — Bhisma Mehta
*Assistant Examiner* — Bradley G Thomas, Jr.

(57) ABSTRACT

The steerable catheter comprises a flexible tube, inside of which different conducts are arranged: one or more conducts for drug administration, vacuum conducts associated with different radiofrequency electrodes, conducts for the conductive wires that conducts the radiofrequency energy to the distal end of the catheter, conducts for the fiber optic cable/s that conducts the laser energy to the distal end of the catheter, a guiding wire for the catherization, and another components; the steerable catheter being connected from the proximal end to a energy unit and other pressure and/or dosing devices; and the steerable catheter optionally including an inflatable balloon to help occluding the vessel; and it also incorporates one or two electrode/s or conductive layer/s in the distal end of the catheter; the objective of the steerable catheter being the obtaining of better results in the embolization and/or chemoembolization treatments.

16 Claims, 8 Drawing Sheets

STEERABLE CATHETER DEVICE AND METHOD FOR THE CHEMOEMBOLIZATION AND/OR EMBOLIZATION OF VASCULAR STRUCTURES, TUMOURS AND/OR ORGANS

This invention pertains generally to the technical sector of the chemoembolization and/or emobilization of vascular structures, of benign, premalignant, or malignant tumours, and/or of partial or complete organs of a patient.

More particularly the present invention relates to a steerable catheter, which comprises the emission of at least energy from radiofrequency source and laser source before, during, and/or after the administration of a chemotherapeutic and/or embolization drug; and also the method of operation of the catheter. Additionally, other types of energies can be also incorporated in the catheter, which are preferably selected from the intense pulse light microwaves (IPL) or the high-intensity focused ultrasound (HIFU).

The purpose of the catheter device is energy transfer to the surrounding tissue in order to involve tissue changes and/or environmental changes, which promotes the effect of the administered drug directly and/or indirectly: directly by changing the drug itself structurally, or indirectly by changing the surrounding tissue in region where the drug was administered. Other changes can result in an increased therapeutic effect, due to induced necroses to tissue, changes in blood flow (increased, decreased and/or stopped), and a better drug control (higher concentration, less drug wash out, less backflow) in the treated area.

Tissue ablations techniques with the assistance of different types of energy sources are well described in literature. These methods were already used in the open surgery and invasive treatment. The simplest example is applying an electric energy source during open surgery for tissue coagulation.

Specifically laser and radiofrequency sources are already used separately in an ablative and non-ablative manner. However, in all these treatment options the energy is used for a direct energy transfer-tissue contact interaction, so the only goal of all systems is tissue denaturation and/or coagulation.

As described in U.S. Patent Application Publication No. 2005/159734A1, it is known an apparatus for treating a biological tissue of a patient in situ comprising an optical fibre for guiding a coherent waveform to a fibre tip for discharge of light energy from said fibre tip in a direction of energy discharge, and a guide tip coupled to said fibre tip.

In U.S. Pat. No. 4,565,200 an electrode system is described in which a single entrance tract cannula is used to introduce an electrode into a selected body site.

In order to occlude the vessel an inflatable balloon is generally used at the distal end of a catheter, as described in U.S. Pat. No. 3,435,826 and U.S. Pat. No. 4,762,130.

Also, in the US Patent Application Publication No. 2006/9404 the radiofrequency treatment combined with pharmaceutical compositions is described to ablate tumour masses by means of a needle having one or more tines, which can comprise a pharmaceutical composition.

Regarding the drug treatments, the present principal problem is the drug wash out and drug control in the treated area, since high concentration and/or high toxic embolic and/or chemotherapeutic drugs cannot be used safely as a systemic and interarterial treatments.

Thus, it exists a patent need to develop a method and apparatus for optimizing the local drug control once the therapeutic was injected in the treated area. For example, connection drugs with the other carriers or to antibodies can be used with the aim of changing the molecules, and these are yet in study.

Nevertheless, tissue interaction for better drug control and/or modification has not been described or known in the hereby-described field. Increasing the drug potentiality by inducing environmental changes for example changing temperature, or inducing a local light source in tissue can induce a better therapeutic effect. Said environmental changes can also comprise those changes of the surrounding tissue by, for example, inducing changes in blood flow in the treated area. These changes can be permanent and/or non-permanent: non-permanent changes can be vasodilatation and/or vasoconstriction, and/or blood extraction in the treated area; and permanent changes can be vaso-occlusion, induced tissue necroses, or changes in permeability of the tissue barriers and/cell barriers in the treated area. All these changes can be induced before, during and/or after drug administration. All the described methods could change the drug-tissue interaction.

Embodiments of the present invention relate to an improved method and apparatus with the aim of obtaining better results in the treatment with embolization and/or chemoembolization.

In addition, the embodiment of the invention relates to a better drug control and/or tissue control in the treated area, to ensure a better drug-energy-tissue interaction. By using these assists better results could be obtained in the treatment of for example vascular malformations in tissues, or the treatment of benign and/or malignant tumours.

Therefore, as a result of the present invention, high concentration and/or high toxic embolic and/or chemotherapeutic and/or immunoactive drugs, which until now cannot be used systemic and interarterial, will be able to be used in a safer way.

Therefore, modification and/or activation of the drug by an energy source will result in a new therapeutic window for the treatment of very aggressive tumours or vascular malformations. For example, accidental drug leakage in the non-therapeutic area will be able to be better avoided. In other cases, by increasing blood flow by vasodilatation it will be able to obtain an increased drug absorption in tissue.

Additionally, these new devices could simplify remarkably the treatment protocols by ensuring complete and effective devices, which can be located in situ in an organ by catherization, and/or by direct puncture of soft tissue or organs, and in which as well as different energy sources as different drugs, and/or vacuum can be administered. Such these technologies will enable to treat a wide range of pathologies with less instrumentation for the patient. By using the catheter of the invention more local invasive techniques in the treated area can be performed through smaller incisions and a smaller amount of catheters, with a lesser morbidity, lesser traumatic to the surrounding tissue and lesser side effects.

Thus, with these new devices better drug and/or environmental control will be obtained with better therapeutic results and better patient satisfaction or patient survival rates in malignant tumours.

The embodiment of the invention is engineered for human use; however, it can be also suitable for other species in vivo and/or in vitro and in the largest sense of the word, and/or in tissue engineering and/or others.

It is an object of the invention to provide a probe for changing the blood flow in the efferent and afferent vascular system (increased, decreased) to obtain a better drug control and/or drug modification.

It is also object of the invention to provide a probe for changing the surrounding tissue by changing their barriers (vessel barrier, tissue barrier, cell barrier).

It is a further object of the invention to provide a probe for changing and/or activating the therapeutic drug. This can be directly and/or indirectly through the tissue interaction.

These and other objects of the present invention will become more apparent from the discussion below.

According to the present invention, a method and apparatus are disclosed which enables reliable and/or controlled destruction of tissue by the combination of a drug, dye and/or the administration in situ of active and/or non active particles and/or substances, liquids, gases and others or a combination of these mentioned above with an energy source and contrasts.

The apparatus comprises essentially a catheter, which incorporates different drug conduits and vacuum conduits associated with different electrodes, radiofrequency conduits, optical fibres and other components, and the apparatus is connected with an energy unit. In addition, an inflatable balloon is provided at the distal end of the catheter to help occlude a vessel. The energy assist embolization catheter embodiments of the invention can also incorporate the necessary devices to introduce the catheter in an anatomical site in the treated area or at a distance of the site. This instrumentation can enable the physician to expose the active distal end in the therapeutic area by different techniques: tunnelling, catherization and/or dissection, and/or direct puncture. In order to place the catheter in the treated area different energy sources and/or energy conduits, which were introduced in and/or built in the catheter can be used. Thereby the physician can dissect, coagulate and ablate tissue with optimum results. Other devices that can be incorporated in the catheter are: a guide wire, sheets, distractors.

The catheter according to the invention comprises an elongated flexible tube inside of which a plurality of conduits and wires go through until the distal end of the catheter: at least one conduit for drug administration, an optical fibre cable inside of which comprises one or more optical fibres to pass on the laser light, and a guiding wire to carry the catherization out. Preferably, one or two electrodes/s or conductive layers can be positioned on the outer surface of the catheter distal end to emit radiofrequency waves generated by a radiofrequency source at the distal end of the catheter. Each of these electrodes is connected to a conductive element, which is electrically coupled to a radiofrequency generator.

Optionally, a guiding mechanism can also be incorporated within the flexible catheter tube; said guiding mechanism being formed of at least one steering or pull cable.

Furthermore, the described catheter can also include at least one inflatable balloon with its corresponding conduits for inflating/deflating said balloon. Each balloon requires at least one conduit to obtain the inflation or deflation of it, which forms an independent lumen.

Alternatively, inside the catheter tube a conduit for a dye or other liquids such as refrigerating fluids to refrigerate the electrodes can be provided.

Alternatively, inside the catheter tube delivery devices for other energies' transmission can be incorporated. These energy sources, which can be connected to the probe, can have different wavelengths, be different types of light sources or be other types of energy.

Therefore, in accordance with the above mentioned, the distal end of said catheter comprises at least one independent lumen for the drug administration, one central lumen for the guiding wire, one lumen for the optical fibre/s and another lumen for the radiofrequency energy wire; and at least one electrode placed on or near to the distal end of the catheter.

The balloon/s quoted above is/are placed in the vicinity of said distal end and can be positioned not only in target tissue or organs, cavities (such the thorax, sinu) or conduits (arterial, venous), but also for example in hepatic duct, or urethra etc. The inflation of the balloon can alter the flow in the conduit, can prevent leakage of an injected agent, or can create a physical separation, compression, or shield in tissue.

Preferably, the electrical wire/s for activating the electrode/s and the optical fibre cable which contains the optical fibre/s will locate close one to each other in order to reduce the catheter tube's diameter and make the catheter compacter and easier to use.

In reference to the radiofrequency source, one or two conduits or lumens for said electrical wires are used, this to use the system as a unique or bipolar unit. If a unipolar configuration is used, the ground electrode is placed apart from the catheter distal end.

Said electrical wire/s may be fabricated from one or more lengths of tubing, secured at to the tube or advantageously at other energy conduits such as an optic fibre.

Different electrodes can be isolated with insulating material. Said electrode can have different configurations on cross-section, and even coiled into a helix. The electrode can be incorporated into a mesh, or can include lengths of sheet or bar material to an other support, having a semicircular configuration or other geometry thereby forming a part of and/or a complete lumen which can be uses for example to mount the optic fibre. Other geometric forms are possible for the electrodes, such as concentric configuration.

The electrode itself can be fabricated from any metal (for example gold, platinum or tungsten), metal deposits over a carrier (gold-plated stainless steel, gold deposited polyamide or platinum deposited polyester). This carrier can be incorporated or be an effective other component of the catheter and can be very malleable, must be resistant to external forces, must bend this allowing catherization.

The catheter has at least one or more optical fibres. These can be in independent conduits or can be coupled. It is important that the light diffusing energy into the human tissue is in a uniform manner. The energy is diffused radially and outwardly in a uniform distribution along the entire length of the fibre assuring a proper heating or energy distribution at the therapeutic end.

The optical fibre will be connected to a laser source, which is located out of the catheter, and in collaboration with the selected connection devices.

At the distal end of the catheter temperature and/or Doppler probes can be associated with the existing electrodes, in order to measure the temperature and the blood flow respectively.

One possible embodiment for a communal lumen where bipolar electrodes are used is providing an inner electrode and an outer electrode of cylindrical configuration at a concentrical position, between of which several optical fibres are arranged.

Another possible embodiment for a communal lumen where bipolar electrodes are used is having two electrodes with U-shaped section situated face to face, in between of which several optical fibres are arranged.

In both previous options, the optical fibres are arranged in the space between the two bipolar electrodes, so acting advantageously as an insulating element for the bipolar electrodes.

Preferably, said steering or pull wire/s, which function is to guide the distal end of the catheter, locate near the electrodes and optical fibres in order to optimize the steering of the distal end. The steering or pull wire end is radio opaque or echo opaque.

Extra markings for navigation and mapping can be added (e.g. for detection by infrared camera, MRI, CT related procedures).

The steerable catheter can also incorporate an information center unit, which is an electronic device that measures different catheter current parameters of the catheter, such as the pipe, the current use or the wave flanges. Said information center unit is located near the proximal end of the catheter and it is connected to the energy generator unit to transmit the measuring parameters to the generator.

The central lumen of the catheter receives the guiding wire for catherization. Through this lumen active or non-active substances can be administered. This part of the catheter can be connected to a volumetric pump for perfusion of the probe or probe cooling or other purposes. Through this conduit measurement probes or energy probes can also be introduced. The connector has a valve mechanism and luer adaptor.

At the proximal end of the catheter the conduits join into a handle that incorporates the different ports to the different units of the catheter, and a steering mechanism of the distal end of the catheter. Certain of these ports incorporate a luer adaptor, or another tubing or an electric, or a fibre, or another connection, capable of transmitting the necessary source of energy or substance.

The handle incorporates at least one or more conduit to supply the energy on the catheter therapeutic end. The conduits are connected to the energy source by a connection device.

The multi-conduit catheter and its additional structures can be fabricated from different raw materials having the desired qualifications, the desired pattern, cross sectional profile, and dimension. It can contain rod, wire, tubes, sheets, ribbons, optical fibres etc. These raw materials can be fabricated by extruding, injection moulding, forging, rolling, casting and others to obtain the right shape and configuration. The different elements of the catheter may be cut from raw material by water jet cutting, laser cutting, US cutting, EDM machining, photochemical etching, or others to obtain the lumens, pores, ports, and other features from the raw material. All the different components of the catheter can be assembled and/or unified by laser welding, adhesive bonding, ultrasonic welding, radiofrequency welding, soldering, spot welding, or other means.

Various components of the probe, which can be fabricated from at least one wire, tube, ribbon, sheet, rod, band or bar of raw material, which were cut the desired configuration, can be thermally changes into the desired 3-dimensional configuration. During the fabrication the components can be stressed into the resting configuration form using mandrels and/or forming fixtures, having the desired resting shape of the puncturing components and heated to a temperature between 300 and 650 degrees Celsius for a predetermined period of time. Once the material has reached the desired temperature for desired period, the component is quenched and chilled by different methods, and/or gases, and/or liquids.

Components from the catheter can have different patterns to allow the correct geometry for assemblage. These can be oval, circular, rectangular, square, trapezoid, and others. These elements can be cut to the desired length and stressed to the desired shape by different manufacturing proceeds as mentioned above.

The different components of the catheter can be tumbled, sand blasted, bead blasted, chemically etched, ground, mechanically polished, electro polished, or otherwise treated to remove any edges and/or procedure a smooth surface.

To tailor the stiffness profile of the components of the catheter, holes notches, cut away areas, and others can be performed. The techniques to perform these changes are described above; and by means of these changes we can change the stiffness profile of regions and/or complete parts of the catheter. These changes can be for example in function of the length of the catheter to reinforce specific regions and/or to customize parts of the catheter. Certain parts of the catheter can be coated with radio or echo opaque materials.

Additional markings can be added in order to make navigation technique possible.

In reference to the tubular shaped body of the catheter, it can be fabricated from a metal, metal alloy, PEBAX®, polyester, polyurethane, urethane, silicone, polyamide, other thermoplastic, thermoset plastic, or elastomer, or braided metallic wires covered with polymer. Said tubing(s) may have a circular, elliptical, or any geometry, this depending on the stiffness, configuration of the different parts, and assemblage.

In reference to the inflatable balloon, the substance to be used in the inflatable balloon conduits and balloon can be a gas or liquid or a mixture. The liquid can be an active agent, or can be a substance absorbing light or diffusing light. It can be air, water, oil, contrast agents, perflueocarbons, saline solutions, dyes, etc.

For deflation and inflation and for the maintenance of a calibrated volume there is at the end of the in(de)flate member a valve. On the valve a syringe or other calibrated dispenser can be connected, the dispenser can work by volume or by pressure. Advantageously by using pressure and volume data information can be obtain of the target area.

The shaft of this part of the catheter can be manufactured of different materials selected in the group of the stainless steel, polyamide, polyethylene, polystryren, polycarbonate, extrudable polymer, thermoplastic, silicone, rubber, composite, brass, titanium, aluminium, ceramic etc; This list is not limitative.

The inflatable member can be made of an inelastic or elastic material. In case of elastic material the balloon can take the shape of the target tissue, conduit, or space. In case of an inelastic configuration the tissue, or conduit, or space will take the form of the inflated member. Said inflated member can have any configuration in size or shape, and preferably its shape can be spherical, ovoid, elliptical, cylindrical and other. The wall of the balloon must be supple enough to change in size and configuration as the introduced substance volume is changed, but at the same time it must be also stiff enough to be manipulated during instrumentation and placement, and finally it must be resistant to high pressure and temperature.

The inflatable member can be manufactured from material selected in the group of silastic, silicone, c-flex, polyester, mylar, polyurethane, polyvinyl, polyethylene, latex, rubber; this list is not limitative.

The following is descriptive of certain embodiments of the invention. The descriptive cannot be taken in the limited sense, but is made to illustrate the general principles of the invention.

A list of the various references used to describe the embodiments carried out on the apparatus of the present invention follows:
(10) catheter;
(11) proximal end;
(12) distal end;
(13) handle;
(14) conduit for the balloon;
(15) guiding wire;

(16) electrical connector;
(17) radiofrequency source;
(18) balloon connector;
(19) pressure device connector;
(20) pressure device;
(21) conduits for drug;
(22) drug connector;
(23) drug applicator;
(24) optical fibre conduit;
(25) optical fibre connector;
(26) laser energy source;
(27) catheter tube;
(28) inflatable balloon;
(29) optical fibre;
(30) electrode;
(31) central opening;
(32) side opening;
(33) steering cable;
(34) energy lumen;
(35) outer electrode;
(36) inner electrode;
(37) U-shaped section electrode;
(39) energy connector;
(40) conduit for dye;
(41) steering mechanism;
(42) valve;
(43) volumetric pump;
(44) central lumen for guiding wire;
(45) electric conduits; and
(46) radiofrequency lumen.

Figure 1A:
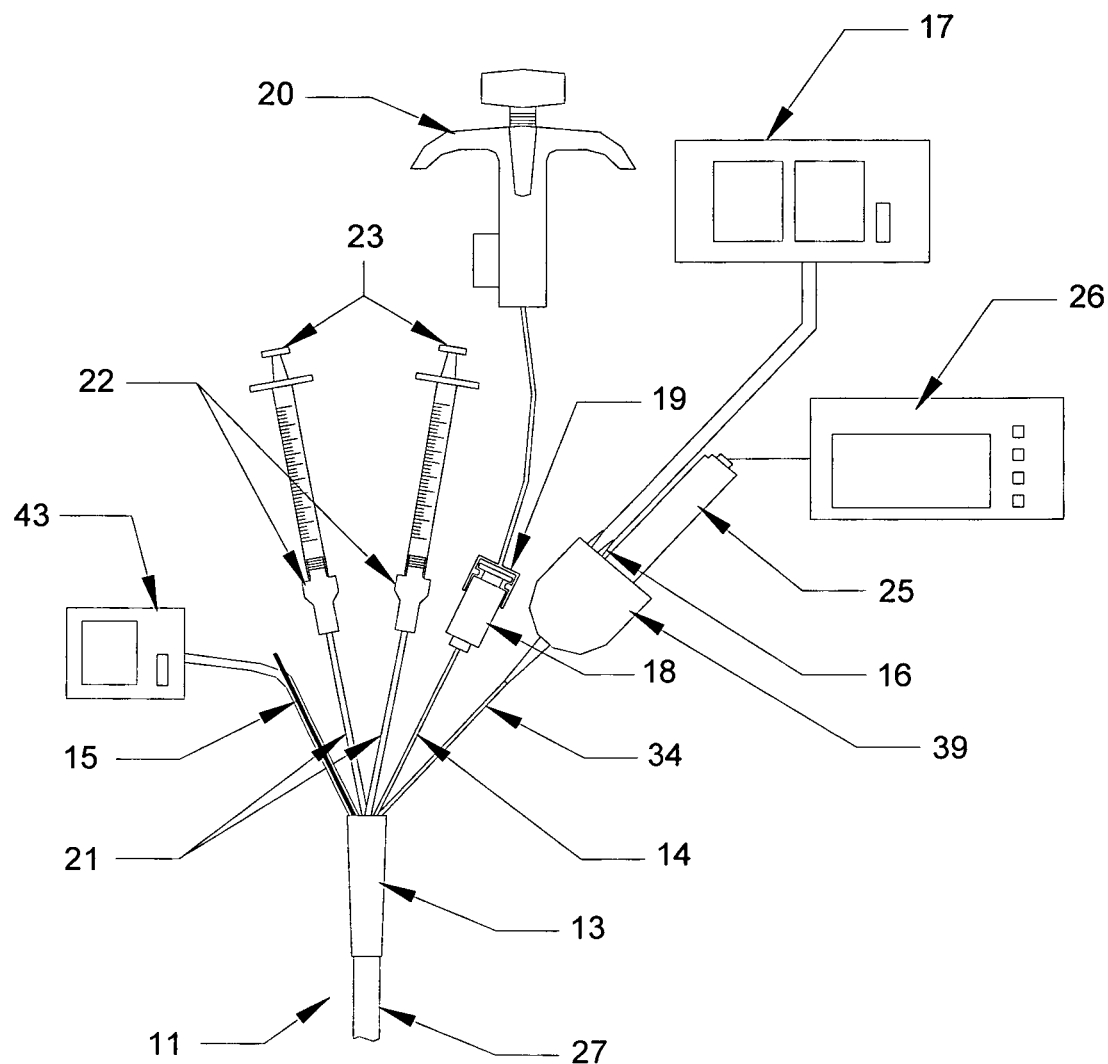
FIG. 1a-1c depicts a partial view of three different embodiments of the proximal end (11) and the handle (13) of a catheter embodiment of the invention.
Figure 1B:
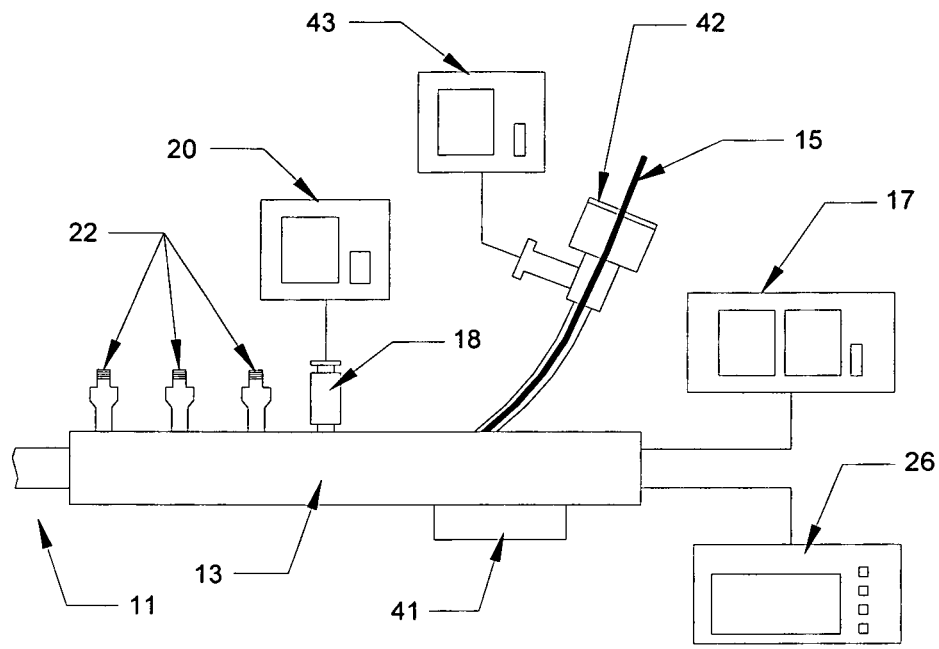
Figure 1C:
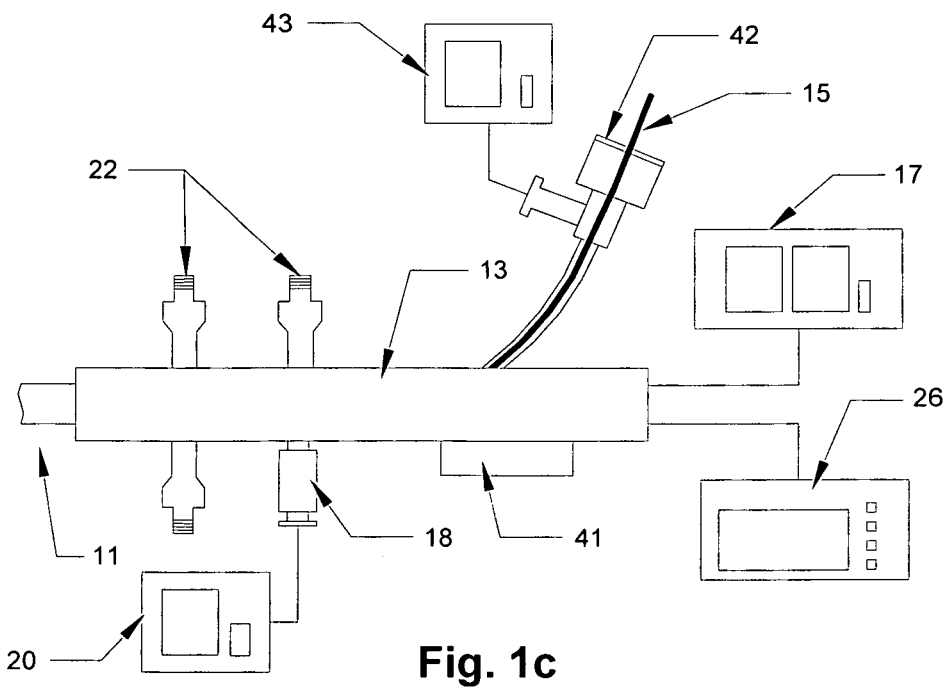

FIGS. 1a-1c illustrate the catheter proximal end (11) comprising a handle (13), at one end of which the catheter tube (27) is connected and at the opposite end the different ports (47) where the different conduits and wires are connected, in order to arrange all the elements in the proper way within the catheter tube (27). At least a conduit (21) for drug administration, an energy conduit (34) for containing the energy elements and a guiding wire conduit (44) for containing the guiding wire (15) are steered towards the interior of the body (27) of the catheter (27). Additionally, a conduit (14) for the inflation/deflation of the balloon (28) can also be incorporated and also a steering mechanism (41).

At the end of the guiding wire conduit (44) for the guiding wire (15) and other substances a volumetric pump (43) is incorporated for perfusion of the probe or probe cooling. Additionally, the respective connector has a valve (42).

At the end of the conduit for the balloon (14) a connector (18) is provided, in order to join said conduit (14) with a pressure device (20), for example a pump or similar, which function is the inflation/deflation of the balloon (28).

At the end of the conduit for the balloon (14) a balloon connector is provided to connect with a pressure device (20), such as a pump or similar, which function is the inflation and the deflation of the balloon depending on the required configuration.

At the end of the energy conduit (34) an energy connector (39) is provided, the inputs of which are an electrical connector (16) and an optical fibre connector (25), which both are also connected to the corresponding energy sources: the radiofrequency source (17) and the laser energy source (26) respectively.

The distribution of the different ports (47) in the handle (13) can be any, for example the ports (47) being arranged in the same side, as it is shown in FIG. 1b, or being arranged in both sides of the handle (13), as it is shown in FIG. 1c.

Figure 2:
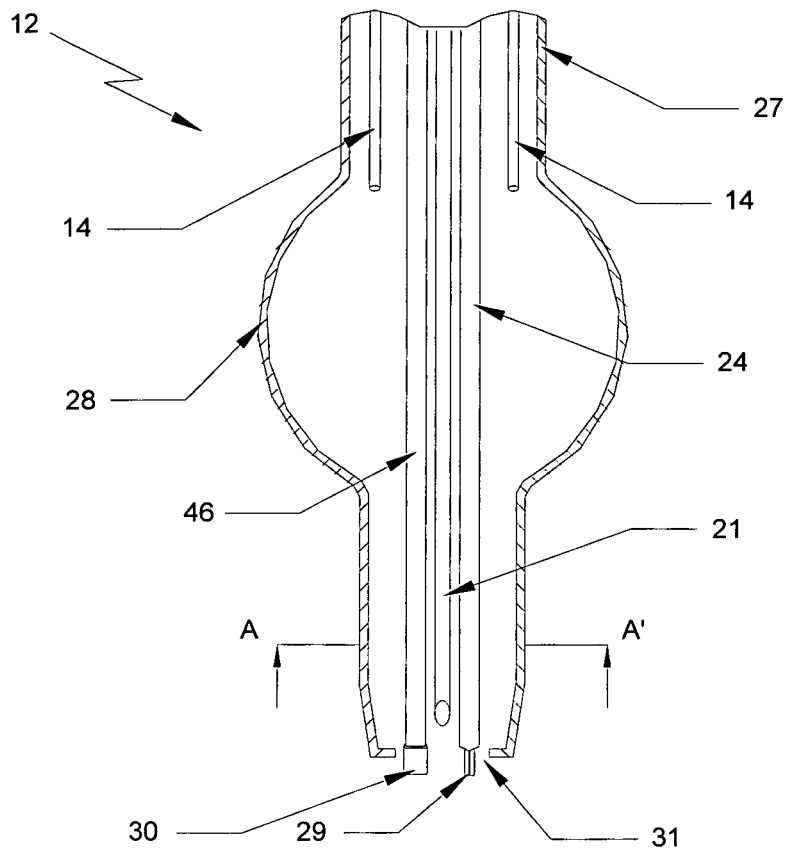
FIG. 2 depicts a longitudinal-sectional view of the distal end (12) of a catheter embodiment of the invention.
Figure 3:
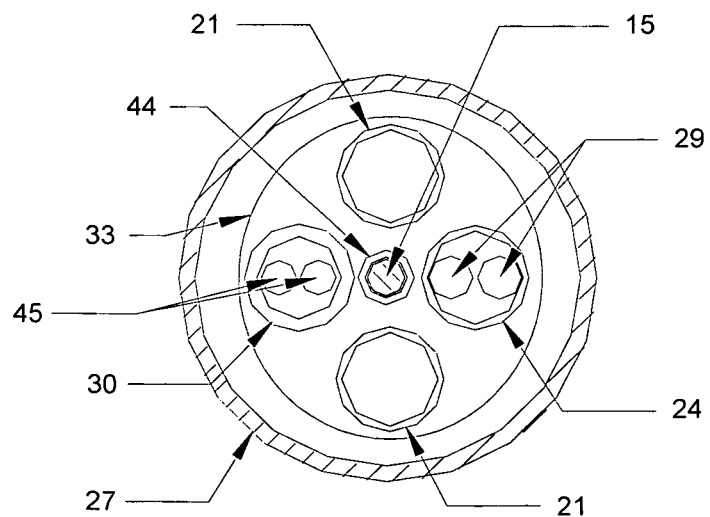
FIG. 3 depicts a cross-sectional view across line A-A' of the embodiment of the invention in FIG. 2.

Referring to the embodiment of a catheter (10) as shown in FIGS. 2-3, the distal end (12) of a steerable catheter (10) may comprise essentially a flexible tube (27) inside of which a plurality of conduits and wires go through, thus forming the multi-lumen catheter. In this particular embodiment of a catheter (10), which is the simplest one, a lumen for drug administration (21), a radiofrequency lumen (46) for the electric conduits (45) for activating the polar electrodes (30), a lumen (24) for the transmission of the laser energy inside of which comprises two optical fibres (29), a central lumen (44) for the guiding wire (15) and a steering cable (33) with a circumferential perimeter that surrounds the rest of the quoted lumens.

Furthermore, in this particular embodiment, an inflatable balloon (28) is also provided, which is inflated/deflated by means of a substance that flows inside the two conduits (14) and being steered by the pressure device (20).

Optionally, inside the catheter tube (27) a lumen for a dye (40) or other liquids, which is not shown in the figures, such as refrigerating fluids to refrigerate the electrode/s can also be incorporated.

The distal end (12) of the catheter (10) has two different openings: two side openings (32) for the drug (21) and dye (40) conduits, and a central opening (31) for the energy conduits (46) and (24) and the wires (15) and (33) located in a central part of the end of the catheter tube (27).

Figure 4:
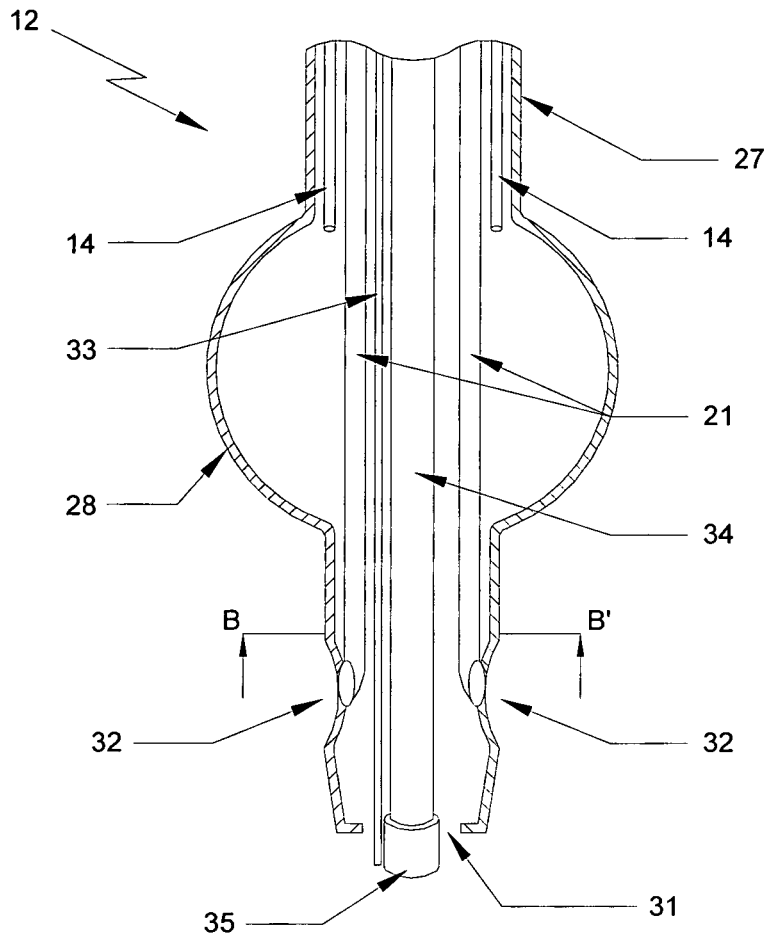
FIG. 4 depicts a longitudinal-sectional view of the distal end (12) of another catheter embodiment of the invention.
Figure 5:
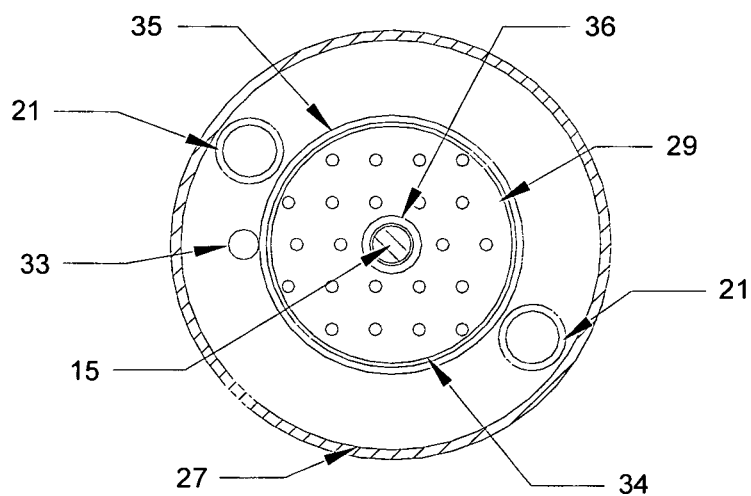
FIG. 5 shows a cross-sectional view across line B-B' of the embodiment of the invention in FIG. 4.

Referring to FIGS. 4-5, there is shown a second example of the distal end (12) of a steerable catheter (10) comprising a flexible tube (27) inside of which a plurality of conduits and wires go through, thus forming at the end a multi-lumen catheter (10). In this embodiment, two conduits for drug (21) are provided, as well as a steering cable (33) and a balloon (28) with its respective conduits (14). However, the special feature of it is the energy lumen (34), which is a communal lumen inside of which there is the central lumen (44) for the guiding wire (15) in a central position surrounded by optical fibres (29). At the end of said energy lumen (34) a bipolar electrode is placed; the inner electrode (36) is the outer wall of the central lumen (44), which is a conductive layer, whereas the outer electrode (35) is located in a concentrical position regarding the inner electrode (36) in the outer layer of the lumen (34). Between the bipolar electrodes (35-36) several optical fibres (29) are arranged, which act as an insulating material.

Figure 6:
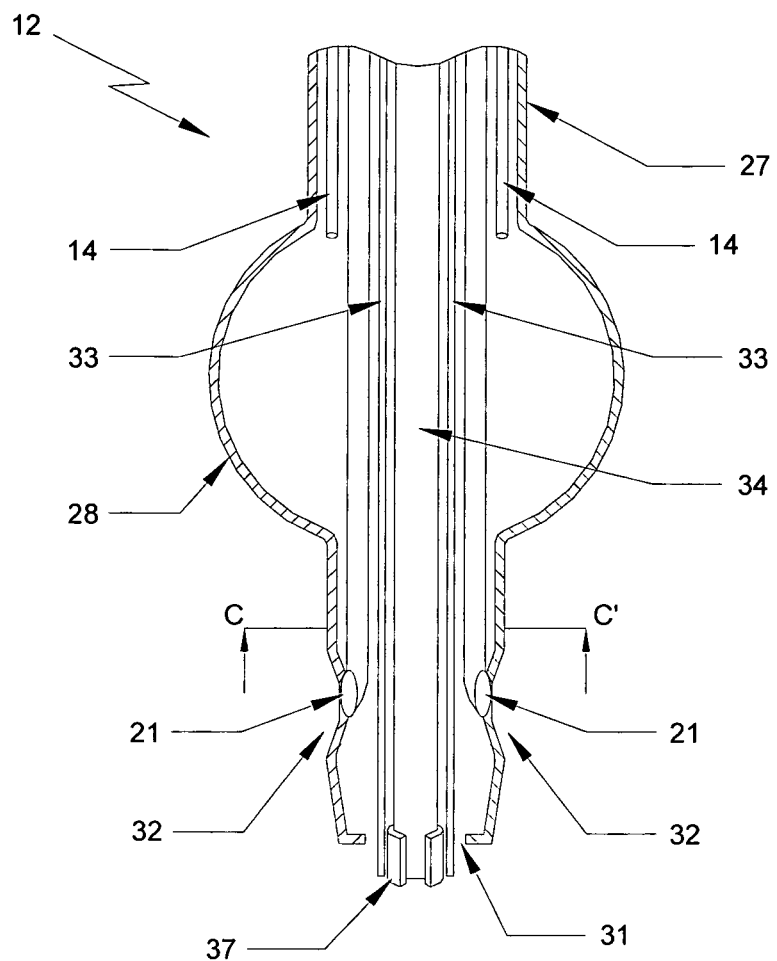
FIG. 6 shows a longitudinal-sectional view of the distal end (12) of further catheter embodiment of the invention.
Figure 7:
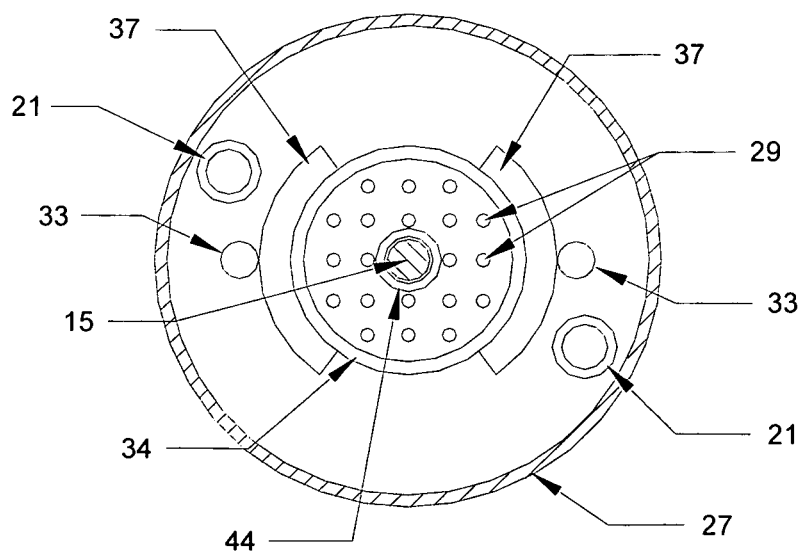
FIG. 7 shows a cross-sectional view across line C-C' of the embodiment of the invention in FIG. 6.

In a variation of this embodiment of the multi-lumen catheter (10), as shown in FIG. 6-7, it also incorporates two conduits for drug administration (21), a balloon (28) with its corresponding conduits (14), two steering cable (33) and a common energy lumen (34). But said common energy lumen (34) has another configuration; the central lumen (44) for the guiding wire (15) is located in a central position and its outer wall is not active. Thus, there are two bipolar electrodes with a U-shaped section (37) configuration and they are located close to the outer surface of the lumen (34), one in front of the other, between of which several optical fibres (29) are arranged.

Figure 8:
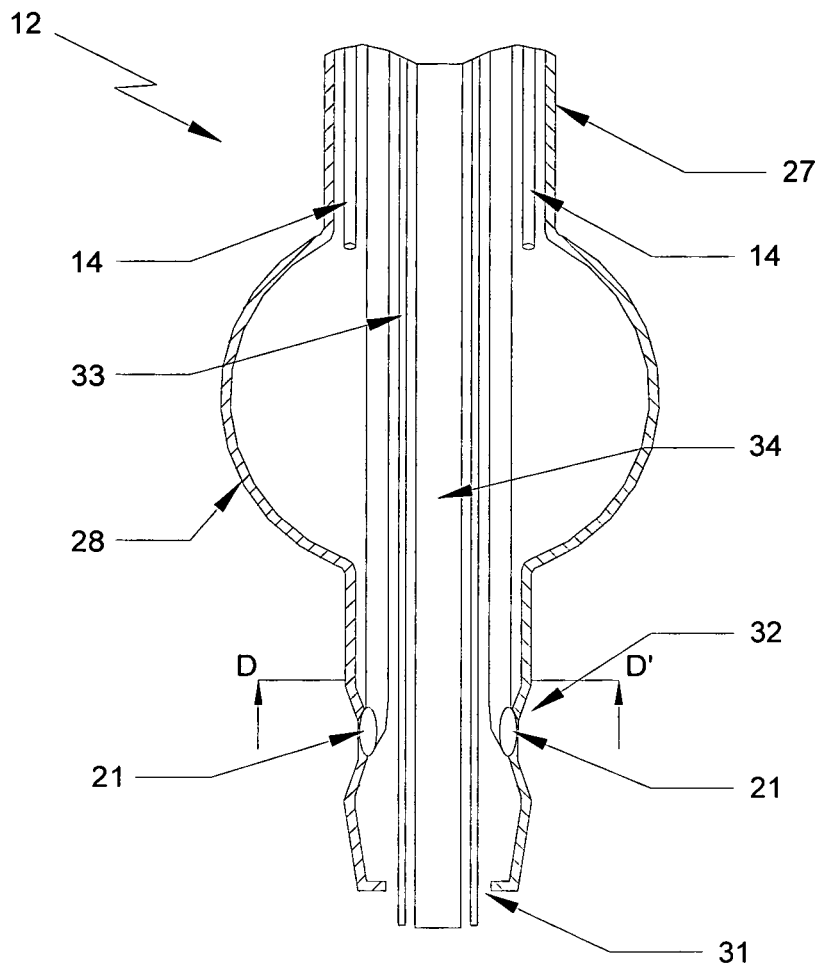
FIG. 8 shows a longitudinal-sectional view of the distal end (12) of further catheter embodiment of the invention.
Figure 9:
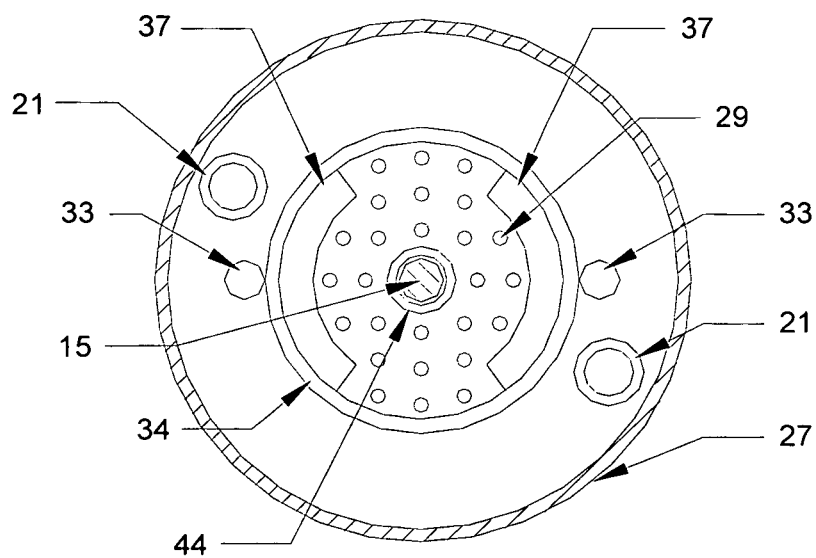
FIG. 9 shows a cross-sectional view across line D-D' of the embodiment of the invention in FIG. 8.
Figure 10:
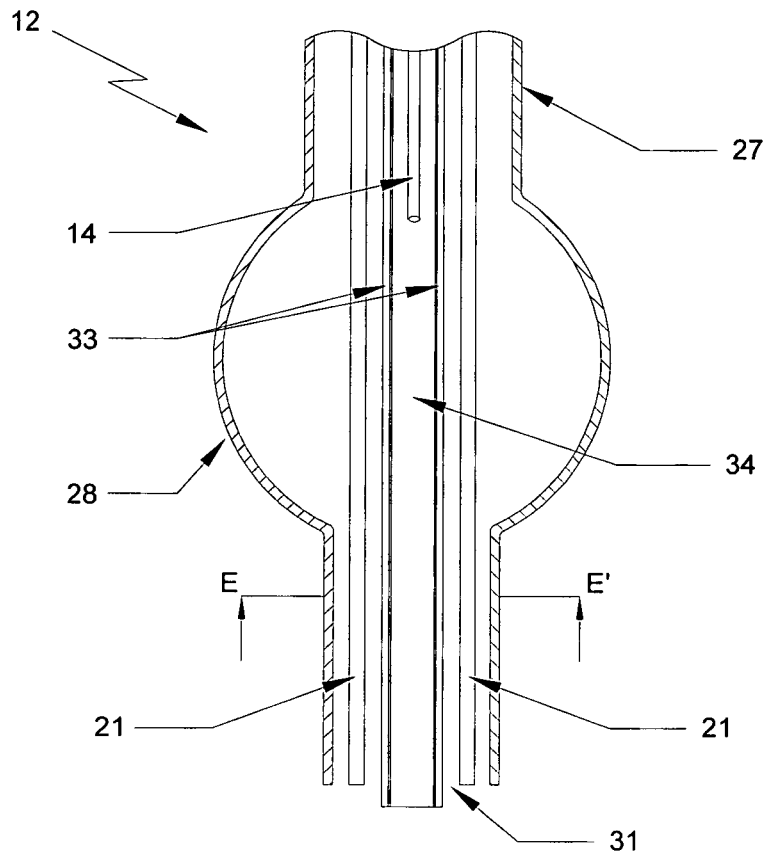
FIG. 10 shows a longitudinal-sectional view of the distal end (12) of further catheter embodiment of the invention.
Figure 11:
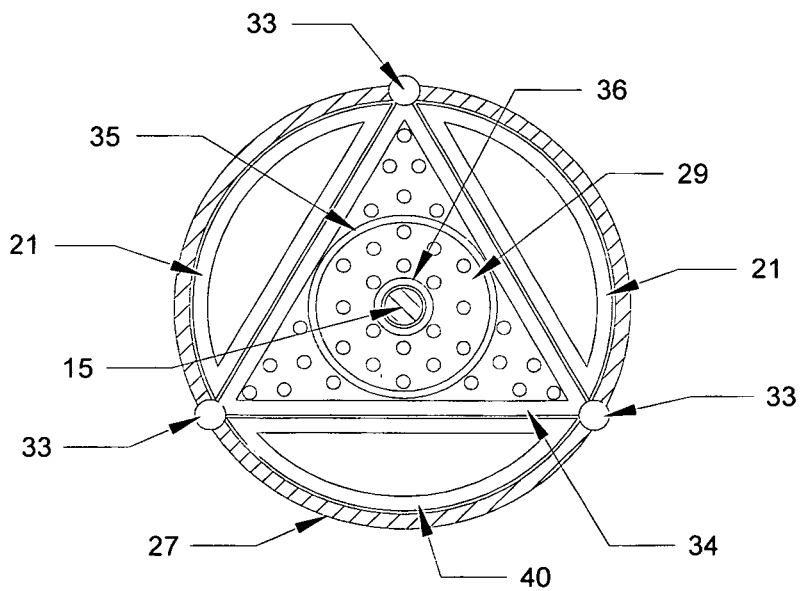
FIG. 11 shows a cross-sectional view across line E-E' of the embodiment of the invention in FIG. 10.

As illustrated in FIGS. 8-9, another embodiment of the multi-lumen catheter (10) is disclosed. It also includes a common energy lumen (34) with a bipolar U-shaped section electrodes (37) and a central lumen (44), but said electrodes (37) are located close to the inner surface of said conduit (34).

In reference to FIGS. 10-13, it is shown two different embodiments, where the drug (21) or dye (40) conducts reach the end of the tubular body (27) of the catheter (10). The distal end (12) of the catheter (10) has four independent lumens: the central one is the energy lumen (34) and the peripheral lumens are for drug (21) or dye (40). The central energy lumen (34) has a symmetric triangular cross section, and in the space between the walls of the triangle and the walls of the tubular body (27) there are three independent lumens with a curved cross section. At the vertexes of said triangle a steering cable (33) is provided in order to guide perfectly the distal end (12) of the catheter (10). The central lumen (44) is situated in a central position of said energy lumen (34) and its outer wall is the inner electrode. The outer electrode is placed within the energy lumen (34) and in a concentrical configuration. Inside of the triangular energy lumen (34) several optical fibres (29) are placed.

Figure 12:
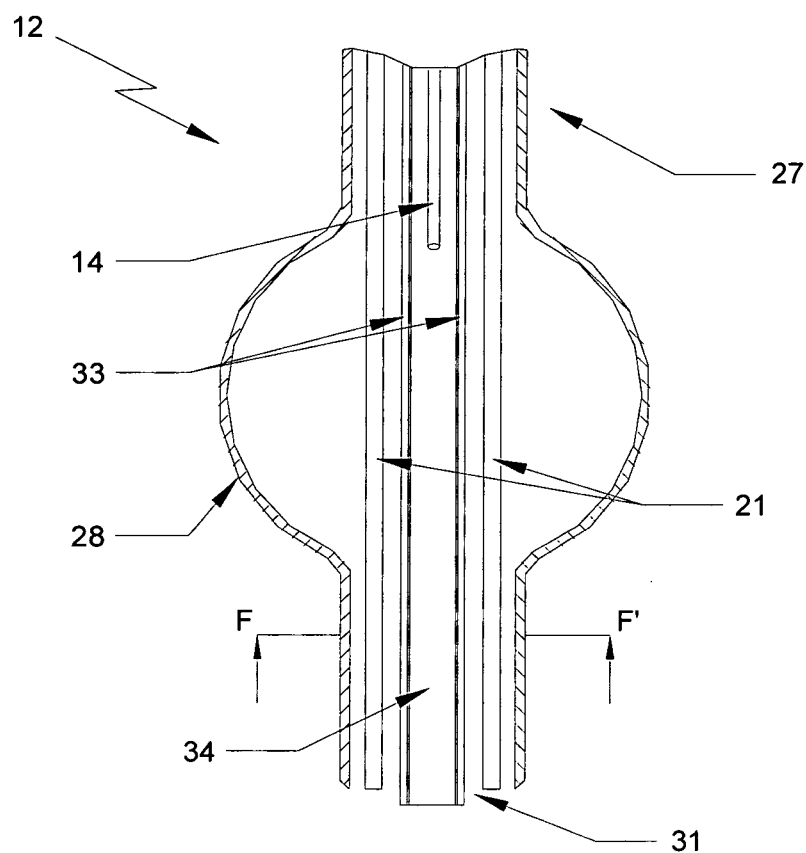
FIG. 12 shows a longitudinal-sectional view of the distal end (12) of further catheter embodiment of the invention.
Figure 13:
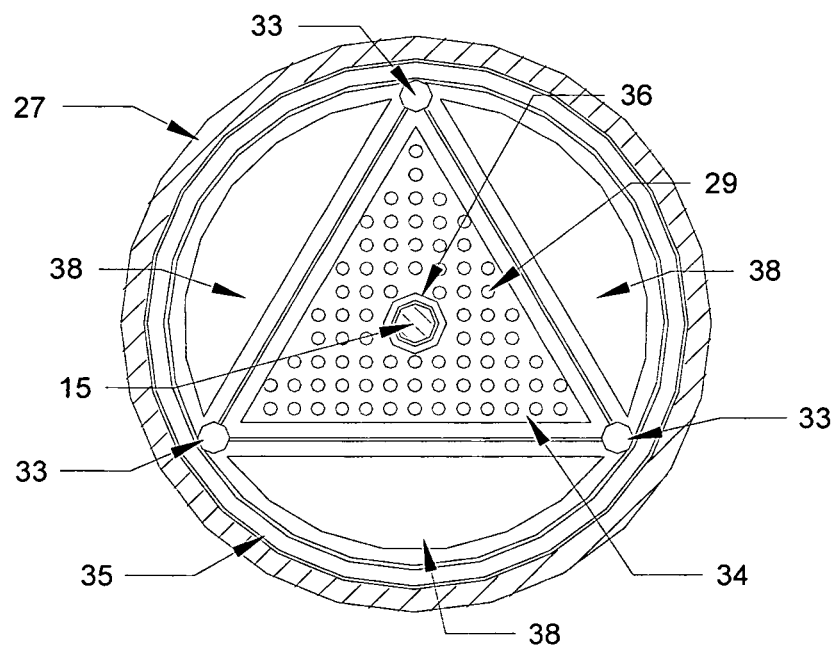
FIG. 13 shows a cross-sectional view across line F-F' of the embodiment of the invention in FIG. 12.

In FIGS. 12-13, the distal end (12) of the multi-lumen catheter (10) has a very similar configuration to the previous embodiment, but with the difference that the outer electrode is placed close to the inner surface of the catheter tube (27).

Although the present invention has been described with reference to the preferred embodiments, workers skilled in the art will recognize that changes may be made in form and detail without departing from the spirit and scope of the invention.

The invention claimed is:

1. A steerable catheter used for the chemoembolization and/or embolization of vascular structures, tumours and/or organs, comprising: a flexible tube including a proximal end and a distal end, said flexible tube enclosing a plurality of lumens, said proximal end of the catheter being attached to a handle including a plurality of ports for the connection and introduction of a plurality of elements in said plurality of lumens, one lumen of said plurality of lumens being used for receiving the guiding wire for the catherization, and optionally the catheter also comprises an obturatory balloon disposed near a distal end of the catheter and another lumen of said plurality of lumens for steering the substance that inflates and deflates said obturatory balloon, said plurality of lumens including at least one lumen for drug administration disposed along the catheter, from said proximal end to said distal end of the catheter, said lumen adapted to transfer drug to the target tissue; and a common energy lumen disposed along the catheter, from said proximal end to said distal end of said catheter, and defined as a triangular cross-section lumen, whereby at the vertexes of the triangular cross-section, a steering cable is provided to guide said distal end of the catheter, whereby in a space between the sides of the triangular cross-section of said common energy lumen and walls of said flexible body there are three independent peripheral lumens each having a curved cross-section, each of said peripheral lumens forming a conduit extending to said proximal end of said flexible body for transferring a substance selected from the group consisting of drugs, liquids, and dyes to the target tissue, whereby in a central position of the interior of said common energy lumen there is a central lumen containing a guiding wire; said common energy lumen further containing at least two energy elements adapted to transfer energy to the surroundings of the target tissue to interact with the administrated drug, said energy elements further defined as having at least one conductive wire adapted to be connected to a radiofrequency source with the selected connection devices, such as a connector and, along said common energy lumen to said distal end of the catheter, and at least one electrode positioned on or near said end of the distal end of the catheter, and at least one fiber optic cable adapted to be connected to a laser source by means of the selected connection devices, such as a connector and, along said common energy lumen to said distal end of the catheter.

2. The steerable catheter of claim 1, further comprising steering system having at least one steering cable in addition to a guidewire, located on the inside of the tubular body of the catheter and extended right to said distal end of the catheter.

3. The steerable catheter of claim 1, wherein at least one drug conduit is connected to a drug applicator with the selected connection devices, such as a connector.

4. The steerable catheter of claim 1, wherein temperature probes and/or Doppler probes can be incorporated at said distal end of the catheter with the electrodes.

5. The steerable catheter of claim 1, further comprising bipolar electrodes, said bipolar electrodes have a circular cross-section and are arranged in concentrical position including an outer electrode of said bipolar electrodes which is located in the inner wall of the triangular cross-section of said common energy lumen of the catheter and an inner electrode of said bipolar electrodes which is the outer wall of said central lumen; and several optical fibers taking up the space between said bipolar electrodes.

6. The steerable catheter of claim 1, further comprising bipolar electrodes, said bipolar electrodes have a circular cross-section and are arranged in concentrical position including an outer electrode of said bipolar electrodes which is located in the outer wall of the tubular body of the catheter and an inner electrode of said bipolar electrodes is the outer wall of said central lumen; and several optical fibers taking up the space between said bipolar electrodes.

7. The steerable catheter of claim 1, wherein the catheter can include a drug concentration device on the delivery site of the drug.

8. The steerable catheter of claim 1, wherein the catheter can be used in the arterial or venous system, in lumen, in cavities, in organs and/or can be directly used by tissue puncture.

9. A method for operating a catheter, comprising:

administering of a chemotherapeutic and/or embolization drug in an area to be treated via at least one lumen of a plurality of lumens enclosed in a flexible tube; and applying a combination of at least two energy sources during and/or after the administration of the drug via a common energy lumen of said plurality of lumens, the common energy lumen defined as a triangular cross-section lumen, whereby at the vertexes of the triangular cross-section, a steering cable is provided to guide a distal end of the catheter, whereby in a space between the sides of the triangular cross-section of the common energy lumen and walls of said flexible tube there are three independent peripheral lumens each having a curved cross-section, each of the peripheral lumens forming a conduit extending to a proximal end of the flexible body, whereby in a central position of the interior of the common energy lumen there is a central lumen containing a guiding wire.

10. The method of claim 9, wherein said two energy sources are radio-frequency signal and laser light energy.

11. The method of claim 10, wherein said laser light energy is generated in a laser generator and is conducted to a distal end of the catheter by means of at least one optical fiber.

12. The method of claim 10, wherein said radio-frequency signal is generated in a radio-frequency generator and is conducted to a distal end of the catheter by means of at least one electrical wire and one electrode.

13. The method of claim 9, wherein said energy sources are selected from a group consisting of intense pulse light energy source, heat energy source, microwaves and high-intensity focused ultrasound.

14. The method of claim 13, wherein said energy sources include a generator and a leading means to a distal end of the catheter.

15. The method of claim 13, wherein said energy sources can be delivered in independent or common lumen.

16. The method of claim 13, wherein said energy sources includes one or more drug and/or embolization catheter(s) and/or a catheter where a vacuum source can be placed.

* * * * *